(12) United States Patent
Heltovics et al.

(10) Patent No.: US 7,041,337 B2
(45) Date of Patent: May 9, 2006

(54) METHODS OF FRAGRANCING A SURFACE

(75) Inventors: Gabor Heltovics, Budapest (HU); Jill Maureen Mattila, Greensboro, NC (US)

(73) Assignee: The Procter & Gamble Company, Cincinnati, OH (US)

( * ) Notice: Subject to any disclaimer, the term of this patent is extended or adjusted under 35 U.S.C. 154(b) by 120 days.

(21) Appl. No.: 10/428,291

(22) Filed: May 2, 2003

(65) Prior Publication Data

US 2004/0091628 A1    May 13, 2004

Related U.S. Application Data

(63) Continuation of application No. PCT/US01/45016, filed on Oct. 31, 2001.

(30) Foreign Application Priority Data

Nov. 3, 2000 (EP) .................. 00650179

(51) Int. Cl.
B05D 1/34 (2006.01)
B05D 1/36 (2006.01)
B05D 5/00 (2006.01)

(52) U.S. Cl. .................. 427/258; 427/402

(58) Field of Classification Search .............. 427/258, 427/287, 288, 402, 417, 445; 424/401, 70.1, 424/76.4; 512/1–27
See application file for complete search history.

(56) References Cited

U.S. PATENT DOCUMENTS

| | | | |
|---|---|---|---|
| 3,939,099 A | | 2/1976 | Tusa et al. |
| 5,135,747 A | * | 8/1992 | Faryniarz et al. ........ 428/313.5 |
| 5,165,915 A | * | 11/1992 | Tokubo et al. .............. 430/544 |
| 5,374,614 A | * | 12/1994 | Behan et al. .................. 512/3 |
| 5,447,784 A | * | 9/1995 | Williams et al. ............. 428/220 |
| 5,861,145 A | * | 1/1999 | Lucas et al. .................. 424/65 |
| 5,871,718 A | * | 2/1999 | Lucas et al. .................. 424/65 |
| 5,942,214 A | * | 8/1999 | Lucas et al. .................. 424/65 |
| 5,968,488 A | * | 10/1999 | Wachter et al. ............... 424/65 |
| 6,033,679 A | | 3/2000 | Woo et al. |

FOREIGN PATENT DOCUMENTS

| | | |
|---|---|---|
| DE | 199 25 971 A1 | 12/2000 |
| EP | 0 303 461 B1 | 8/1988 |
| JP | 58052211 | 3/1983 |
| JP | 62-025973 | 2/1987 |
| JP | 06287127 | 10/1994 |
| JP | 0176587 A | 7/1996 |
| JP | 0183719 A | 7/1996 |
| JP | 0120541 A | 5/1998 |
| WO | WO 95/16432 | 6/1995 |
| WO | WO 98/07405 | 2/1998 |
| WO | WO 98/47478 | 10/1998 |
| WO | WO 98/56341 A1 * | 12/1998 |
| WO | WO 99/43667 | 9/1999 |
| WO | WO 98/47477 | 10/1999 |
| WO | WO 00/67714 | 11/2000 |
| WO | WO 02/08933 A2 | 11/2002 |

* cited by examiner

Primary Examiner—Timothy Meeks
Assistant Examiner—William Phillip Fletcher, III
(74) Attorney, Agent, or Firm—Kenya T. Pierre; Tara M. Rosnell; Brian M. Bolam

(57) ABSTRACT

The present invention provides a method of applying a fragrance to a surface such as skin and/or hair. The method comprises applying to one area of the surface a first composition wherein the first composition comprises at least one first fragrance oil; at least one first cyclic oligosaccharide, wherein the at least one first fragrance oil and the at least one first cyclic oligosaccharide form a complex, which complex is dissolved or dispersed in the first composition; and a first solvent, wherein the first solvent has a dielectric constant at 25° C. of greater than or equal to 43. The method also comprises simultaneously or sequentially, in either order, applying to the one area or an area adjacent thereto a second composition wherein the second composition comprises at least one second fragrance oil; and a second solvent wherein the at least one second fragrance oil is soluble or is dispersed at 25° C. in the second solvent.

24 Claims, No Drawings

METHODS OF FRAGRANCING A SURFACE

CROSS REFERENCE TO RELATED APPLICATION

This is a continuation of International Application PCT/US01/45016 with an international filing date of Oct. 31, 2001.

FIELD OF THE INVENTION

The present invention relates to a method of fragrancing a surface, preferably a cosmetic method of fragrancing a surface of a human or animal body. The method comprises applying to one area of the surface a first composition comprising a solution or dispersion of a complex, the complex comprising at least one first fragrance oil and at least one first cyclic oligosaccharide, in a first solvent or a mixture thereof, followed by simultaneously or sequentially, in either order, applying to the one area or an area adjacent thereto, a second composition comprising a solution or dispersion of at least one second fragrance oil in a second solvent or a mixture thereof. More particularly, this invention relates to a cosmetic method of fragrancing a surface of a human or animal body with new and unique long lasting fragrance character profiles that are a combination of the individual character profiles of the first composition, which provides long lasting fragrance character, particularly top note fragrance character, with periodic fragrance enhancements thereof, and a second composition, which either provides a traditional, optionally balancing, fragrance character or, optionally, provides a long lasting, optionally balancing, fragrance character, with periodic fragrance enhancements thereof. Methods of the present invention are suitable for fragrancing a wide variety of surfaces but particularly the skin and hair.

BACKGROUND TO THE INVENTION

It has long been a feature of many types of compositions, including cosmetic compositions, that they comprise a fragrance oil for the purpose of delivering a pleasant smell. This can improve the overall consumer acceptance of the composition or mask unpleasant odours. In fact, it can be the sole purpose of some compositions to impart a pleasant odour to the skin, hair or other suitable surface.

Fragrance compositions, broadly speaking, comprise a fragrance oil, or a mixture thereof; and a carrier, or a mixture thereof. Each fragrance oil itself usually comprises many different perfume raw materials with each perfume raw material differing from another by several important properties including character, volatility, olfactory detection (known as the odour detection threshold) and the like. By bearing in mind these different properties, and others, it is possible for highly skilled perfumers to blend different perfume raw materials to develop a fragrance oil with a specific overall character profile. It is usual that the character is designed to develop, alter and mature over time as the different perfume raw materials evaporate from the surface and are detected by the user. For example, perfume raw materials which have a high volatility are commonly used within a fragrance oil to give light, fresh, fruity, citrus, green or delicate floral characters to the fragrance oil, which fragrance characters are detected soon after application. Such materials are usually referred to in the field of fragrances as "top notes". By way of a contrast, the less volatile perfume raw materials are typically used to give characters such as musk, sweet, balsamic, spicy, woody or heavy floral to the fragrance oil which, although they may be detected soon after application, also last for longer. These materials are usually referred to as "middle notes" and/or "base notes".

To date, one of the limiting factors for perfumers when designing specific fragrance characters has been the physical characteristics of the perfume raw materials. As such, it has only been possible to develop fragrance oils which impart a "top note" character for a short period of time. This is because the top note perfume raw materials are highly volatile and therefore rapidly evaporate from the surface. Therefore, any lasting element of a fragrance has been achieved by using middle and base notes, which in turn restricts the achievable character. Blending of higher levels of top note perfume raw materials into a fragrance oil does not improve the long lasting nature of the "top note" fragrance character, but instead may result in a stronger initial burst of "top note" fragrance character which still quickly evaporates.

It is known that consumer preference for fragrance compositions is mostly driven by the initial "top note" fragrance character impression, so that it is desired to prolong the "top note" character impression over time. It is therefore desirable to have a method of fragrancing a surface, in particular, skin and/or hair, wherein the user perceives a long lasting overall fragrance character combination arising from the respective fragrance characters of the first and second compositions, which is not achievable by conventional perfumery means. This allows the formulator to select, for example, specific desired fragrance characters for complexing in the first composition, so as to provide those desired, preferably "top note", fragrance characters over time from the first composition, and to select balancing fragrance characters for release from the second composition. Furthermore, it would be advantageous to create a method of fragrancing a surface, in particular skin and/or hair, wherein one or several well recognised fragrance characters, and particularly "top note" fragrance characters, are combined from the respective fragrance characters of the first and second compositions and are maintained over a substantial period of time, such that unique overall long lasting, "top, middle and base note" character combinations are created. Finally, it would be advantageous to develop a kit or package for use with such a method wherein the consumer is able to use different compositions within the kit or package to create fragrances with different fragrance character combinations.

In the past, many attempts have been made to alter and prolong the volatility profiles of fragrance oils to extend the overall fragrance effect within many types of compositions. For instance, the fragrance oil may be formulated to include a higher proportion of perfume raw materials with a low volatility, i.e. of "middle and base note" character. However, as discussed above, this restricts the fragrance character that can be achieved over time. Another approach has been to chemically, and reversibly, modify the perfume raw materials to form a pro-perfume compound as disclosed in patent applications WO 98/47477; WO 99/43667; WO 98/07405; WO 98/47478; all of which are incorporated herein by reference. The resultant pro-perfumes are not themselves volatile but, after the chemical modification is reversed, usually by hydrolysis upon application to the surface, the perfume raw material is released and can then evaporate in the usual way. In these applications, the release rate of the perfume raw materials is controlled by the reaction rate for transforming the pro-perfume to perfume raw material. Whilst pro-perfumes enable the release of a specific perfume raw material to be delayed, it is impractical to use them to stagger the release of materials such that unique fragrance character combinations are achieved over time.

Further disclosures have discussed improving the overall longevity of a fragrance by delaying the evaporation of the fragrance oil(s), for example, by encapsulating the perfume raw materials (disclosed in JP-A-58/052211, EP-A-303, 461); absorbing the materials onto a surface, for example, by using carbon or zeolites (disclosed in U.S. Pat. No. 6,033, 679); occluding the release of the perfume raw materials, for example, by the formation of a film (disclosed in U.S. Pat. No. 3,939,099); and complexing the perfume raw materials, for example, by using cyclic oligosaccharides. The prior art on this latter method includes JP-A-6/287127 and JP-A-8/176587 which disclose use of hydroxyalkylated cyclodextrins within cosmetic, single phase, alcoholic based solutions or dispersions to sustain the effect of the fragrance; and JP-A-8/183719 and JP-A-10/120541 which disclose a combination of cyclodextrin encapsulated fragrance and non encapsulated fragrance within a solid, liquid or aerosol deodorant composition for prolonging the fragrance duration to at least 2 hours, all of which are incorporated herein by reference. Cyclodextrins have also been used with fragrances within cosmetic compositions to improve the solubility of the fragrance oils within the base matrix. The prior art in this area includes JP-A-62/161720 and JP-A-63/192706 which disclose the use of cyclodextrins in fragranced water based compositions. It is expected that these compositions will also have some degree of sustained fragrance release although this is not commented upon in either of these applications.

Whilst the compositions and disclosures of the prior art provide useful teachings for prolonging the fragrance character of a cosmetic composition as a whole, these approaches still have limitations. The cyclic oligosaccharide(s), when used in the traditional way in a single phase solution, interact with a broad range of perfume raw materials present, including "top, middle and base notes", thereby prolonging the overall character of the whole fragrance and not that of any one character specifically. Furthermore, the prior art does not teach how to develop a method for fragrancing a surface, in particular skin and/or hair, which can achieve prolonged enhancement of, for example, specific fragrance characters delivered from the first composition, for example, specific "top note" fragrance characters, in combination with the same or another fragrance character delivered from the second composition, to achieve a unique combined fragrance character profile over time.

Surprisingly, it has now been found that a method for fragrancing a surface, preferably skin and/or hair, which method comprises applying to one area of the surface, preferably skin and/or hair, a first composition comprising a solution or dispersion of a complex, the complex comprising at least one first cyclic oligosaccharide and at least one first fragrance oil, the complex being dissolved or dispersed in a first solvent, or mixture thereof, in which the first solvent or mixture thereof has a dielectric constant at 25° C. of greater than or equal to 43, preferably greater than or equal to 45, followed by simultaneously or sequentially, in either order, applying to the one area or an area adjacent thereto, a second composition comprising a solution or dispersion of at least one second fragrance oil which may be the same or different from the at least one first fragrance oil, optionally, but not necessarily, at least one second cyclic oligosaccharide which may be the same or different from the at least one first cyclic oligosaccharide, in a second solvent, or a mixture thereof, long lasting fragrance and/or unique character combinations can be created by the appropriate selection of first and second fragrances, which combinations would not have been possible to develop using traditional perfumery. In addition, it has also been found that, once the surface has been fragranced according to the method above, fragrance release from the first composition (and the second composition, if the second composition additionally comprises at least one second cyclic oligosaccharide) can be enhanced over time, either naturally (as fragrance blooms) or deliberately (as fragrance refreshings), to release periodic and unexpected blooms or refreshings, as appropriate, of the specific one or several fragrance characters from the first composition and from the second composition, if the second composition additionally comprises at least one second cyclic oligosaccharide.

This invention can be further enhanced by selecting different fragrance oils for each of the first and second compositions such that they impart different, preferably balancing, desired characters to the overall impression perceived by the consumer. In addition, by using high odour impact "top note" perfume raw materials in the first composition, the user experiences both long lasting and periodic enhancements of "top note" fragrance character throughout usage.

The invention can be enhanced still further by optionally incorporating at least one second cyclic oligosaccharide into the second composition, which, whilst not wishing to be bound by theory, is believed to form a complex association with the at least one second fragrance oil upon the surface. Addition of at least one second cyclic oligosaccharide to the second composition further acts to delay the release, and enables periodic enhancement, of the second fragrance character as a whole. Again, by careful selection of the perfume raw materials of the second composition, and in conjunction with the fragrance character combination from the first composition, the desired overall fragrance character can be achieved.

Finally, this invention can be enhanced even further by the development of kits and delivery packages wherein the user is able to use a variety of different first and/or second compositions to create his/her own fragrance character combination.

It is an object of the present invention to provide a method of fragrancing a surface, preferably skin and/or hair, which imparts to the user a fragrance character combination, of a long lasting fragrance character, particularly, a "top note" fragrance character, from the first composition, combined with a balancing fragrance character from the second composition, throughout usage. It is a further object of this invention to provide a method of fragrancing a surface, preferably skin and/or hair, which produces noticeable enhancements of fragrance character throughout usage. These, and other objects of this invention, will become apparent in the light of the following disclosure.

SUMMARY OF THE INVENTION

The present invention relates to a method of applying a fragrance to a surface, preferably skin and/or hair, wherein the method comprises:

a) applying to one area of the surface a first composition wherein the first composition comprises:
  i) at least one first fragrance oil;
  ii) at least one first cyclic oligosaccharide, wherein the at least one first fragrance oil and the at least one first cyclic oligosaccharide form a complex, which complex is dissolved or dispersed in the first composition; and iii) a first solvent, or a mixture thereof, wherein the first solvent, or the mixture thereof, has a dielectric constant at 25° C. of greater than or equal to 43, preferably greater than or equal to 45;

b) simultaneously or sequentially, in either order, applying to the one area or an area adjacent thereto, a second composition wherein the second composition comprises:

i) at least one second fragrance oil; and ii) a second solvent or a mixture thereof, wherein the at least one second fragrance oil is soluble or is dispersed at 25° C. in the second solvent or the mixture thereof;

with the proviso that, when the second composition is applied after the first composition to the one area, the first solvent or the mixture thereof and the second solvent or the mixture thereof have a composite dielectric constant, at 25° C., of greater than or equal to 43, preferably greater than or equal to 45, immediately after application of the second composition; and with the further proviso that, when the second composition is applied before the first composition to the one area, the second solvent or the mixture thereof either has, or is permitted to develop, a dielectric constant such that, when the first composition is applied onto the second composition, the composite dielectric constant at 25° C. is greater than or equal to 43, preferably greater than or equal to 45, immediately after application of the first composition.

DETAILED DESCRIPTION OF THE INVENTION

All percentages and ratios used herein are by weight of the total first or second composition, as appropriate, and all measurements made are at 25° C., unless otherwise designated. Unless otherwise indicated, all percentages, ratios and levels of ingredients referred to herein are based on the actual amount of the ingredient, and do not include solvent, fillers or other materials which may be combined with the ingredient in commercially available products.

All publications cited herein are hereby incorporated by reference in their entirety, unless otherwise indicated.

The term "cosmetically-acceptable," as used herein, means suitable for use in contact with a human or animal surface such as skin without undue toxicity, incompatibility, instability, allergic response, and the like.

The term "composite dielectric constant" as used herein, means the weighted average of the dielectric constant contributed by the first solvent or the mixture thereof and the dielectric constant contributed by the second solvent or the mixture thereof. The composite dielectric constant is, therefore, the dielectric constant of the mixture, in the desired respective weight ratios, of the first and second compositions, immediately after application, to the same area, of the later applied of the first and second compositions.

As used herein, the term "soluble" means at least about 0.1 g of solute dissolves in 100 ml solvent(s), preferably at least about 1 g of solute per 100 ml solvent(s), at 25° C. and 1 atm pressure.

The elements of this method are described in more detail below.

Method

The present invention relates to a method of applying a fragrance to a surface, preferably skin and/or hair, wherein the method comprises:

a) applying to one area of the surface, preferably skin and/or hair, a first composition wherein the first composition comprises:

i) at least one first fragrance oil;

ii) at least one first cyclic oligosaccharide, wherein the at least one first fragrance oil and the at least one first cyclic oligosaccharide form a complex, which complex is dissolved or dispersed in the first composition; and iii) a first solvent, or a mixture thereof, wherein the first solvent, or the mixture thereof, has a dielectric constant at 25° C. of greater than or equal to 43, preferably greater than or equal to 45;

b) simultaneously or sequentially, in either order, applying to the one area or an area adjacent thereto, a second composition wherein the second composition comprises:

i) at least one second fragrance oil; and ii) a second solvent or a mixture thereof, wherein the at least one second fragrance oil is soluble or is dispersed at 25° C. in the second solvent or the mixture thereof;

with the proviso that, when the second composition is applied after the first composition to the one area, the first solvent or the mixture thereof and the second solvent or the mixture thereof have a composite dielectric constant, at 25° C., of greater than or equal to 43, preferably greater than or equal to 45, immediately after application of the second composition; and with the further proviso that, when the second composition is applied before the first composition to the one area, the second solvent or the mixture thereof either has, or is permitted to develop, a dielectric constant such that, when the first composition is applied onto the second composition, the composite dielectric constant at 25° C. is greater than or equal to 43, preferably greater than or equal to 45, immediately after application of the first composition.

It is believed that the first and second compositions for use in the method of the present invention contribute to the overall fragrance character combination in different ways. As a result, the properties and character of each can be enhanced individually to develop unique fragrance character combinations.

While not wishing to be bound by theory, it is believed that, within the second composition, in its broadest aspect, the second solvent phase delivers the fragrance traditionally, i.e., as it is applied to the surface, the second solvent evaporates leaving the fragrance oil on the surface from which, as the different perfume raw materials evaporate over time according to their inherent volatility, an underlying fragrance character develops. However, within the first composition, the at least one first fragrance oil exists as a formal complex with the at least one first cyclic oligosaccharide in the first solvent matrix, which complex acts to retard the volatisation of the perfume raw materials of the at least one first fragrance oil after application to the surface. This complex is broken down in one of several ways. Firstly, it can slowly degrade over time either as a result of thermodynamic decomposition or, alternatively, as a result of partial or complete dissolution caused by moisture from either the surface (especially the skin) and/or the environment and the like. This slow degradation results in delayed and gradual release of the first fragrance. Provision of the first fragrance as a formal complex in the first composition, i.e., separate from the second composition, enables the formulator to select and complex specific desired fragrances within the first composition, whilst, in parallel, the formulator can provide, preferably, balanced fragrances from the second composition. Secondly, the first fragrance-first cyclic oligosaccharide complex of the first composition can be more rapidly degraded, or "activated", to produce a noticeable enhancement of fragrance release. This can be achieved by increasing the natural decomposition rate by the application of water either naturally, by breathing thereon or by sweating, or artificially, by spraying on a mist and the like. This "activation" results in the user experiencing a noticeable enhancement of first fragrance character from the first composition which adds to the overall character of the fragrance combination as a whole. Surprisingly, it has been found that it is possible to "activate" this complex, and thus generate fragrance enhancements, several times during usage.

Optionally, the second composition additionally includes at least one second cyclic oligosaccharide. While not wishing to be bound by theory, it is believed that, in such optional second compositions, the second fragrance oil and the second cyclic oligosaccharide form an association only on the surface, thereby retarding volatisation of the perfume raw materials of the at least one second fragrance oil. As for the first formal complex described above, this association can be slowly degrade over time and can, if desired, be more rapidly degraded or "activated" to enhance the second fragrance release. Thus, in its broadest aspect, the formulator selects second fragrance(s) for release, in the traditional manner, from the second composition as described above or, optionally, selects second fragrance(s) for release from such associations over time, with the capability of achieving fragrance enhancements for the second fragrance character, if desired.

It will, therefore, be appreciated that the method of the present invention allows the formulator considerable scope in devising a specific long lasting first fragrance character, namely, by separately complexing those specific fragrance characters in the first composition, whilst providing a balancing or corresponding second fragrance character in a second composition, the second composition either delivering the second fragrance character in the traditional manner or, optionally, delaying volatisation by forming an association on the surface. Similarly, the method of the present invention allows the consumer considerable scope in customising the perceived fragrance by applying varying amounts of the same or different first and second compositions.

The first and second compositions of the method of the present invention can be applied to adjacent areas of the surface either together or sequentially in either order. If the first and second compositions are applied sequentially (in either order) to adjacent areas, it is preferred that they are applied within 60 minutes of each other, preferably within 30 minutes of each other and more preferably within 10 minutes of each other. If the first and second compositions are applied sequentially to the one area (the same area), it is preferred that they are applied within 30 seconds to 60 minutes of each other, preferably within 30 seconds to 30 minutes of each other and more preferably within 30 seconds to 10 minutes of each other. Once applied, it is possible to renew either composition by the later application of an additional amount of the first composition, the second composition, and mixtures thereof.

It is highly preferred that, if the compositions are applied sequentially to the same area, then the second composition is applied first followed by the first composition. While not wishing to be bound by theory, it is believed that prior application of the second composition, followed by, if necessary, a delay, allows the second solvent(s) to develop a dielectric constant (by, for example, evaporation) which yields a composite dielectric constant of the overall composition, sufficient to maintain the stability of the complex of the first composition. It is even more highly preferred that, if the weight ratio of the first to second compositions is greater than 1:2, the second composition should be applied first, followed by, after a delay of 30 seconds to 60 minutes, the first composition.

It is important that the compositions are separately applied so that the two compositions only minimally mix, preferably do not mix at all, prior to application onto the surface, in order to prevent potentially premature decomposition of the complex of the at least one first cyclic oligosaccharide and the at least one first fragrance oil. In a further enhancement of the method described herein, one or more of the first and second compositions can be used over time to renew the original application by activating periodic blooming or refreshing, such that the fragrance can adapt and alter over time.

For the method described in the present invention, it is preferred that the weight ratio of the first composition to the second composition is from about 1:99 to about 99:1, preferably from about 1:50 to about 50:1, more preferably from about 1:25 to about 25:1, even more preferably from about 1:10 to 10:1 and most preferably about 1:1.

The method is preferably used for providing fragrance to a suitable surface. As used herein, the term "suitable surface" means any surface to which the present compositions may be applied without an unduly adverse effect. Suitable surfaces include, but are not limited to, skin or hair, especially skin. Other suitable surfaces include, but are not limited to, paper, glass and/or cloth substrates, as well as, work surfaces such as laminates and the like. The compositions for use in the method of the present invention may be used in a conventional manner for fragrancing a suitable surface. An effective amount of the first and second compositions, typically from about 1 µl to about 1000 µl, preferably from about 10 µl to about 250 µl, more preferably from about 25 µl to about 1001 µl, is applied to the surface.

As used herein, the term "bloom" means a fragrance enhancement which is unintended by the user, for example, when the user unintentionally breathes on the first composition or when the user sweats.

As used herein, the term "refresh" or "refreshing" means a fragrance enhancement which is intended by the user, for example, when the user is instructed by, for example, an accompanying instruction sheet, either to breath on the first composition or to spray water or the like thereon.

The term "fragrance enhancement" as used herein, is intended to embrace both fragrance blooms and fragrance refreshings as defined hereinabove.

First Composition

First Fragrance Oil

The first composition for use in the method described herein preferably comprises from about 0.001% to about 20%, preferably from about 0.005% to about 15%, more preferably from about 0.01% to about 7%, and most preferably from about 0.5% to about 5%, by weight of the first composition, of at least one first fragrance oil.

As used herein, the term "fragrance oil" relates to a perfume raw material, or mixture of perfume raw materials, that is/are used to impart an overall pleasant odour profile to a composition. As used herein, the term "perfume raw material" relates to any chemical compound which is odiferous when in a free or un-entrapped state. In addition, "perfume raw materials" have a ClogP value preferably greater than about 0.1, more preferably greater than about 0.5, even more preferably greater than about 1.0. As used herein, the term "ClogP" means the logarithm to base 10 of the octanol/water partition coefficient. This can be readily calculated from a programme called "CLOGP" which is available from Daylight Chemical Information Systems Inc., Irvine Calif., USA. Octanol/water partition coefficients are described in more detail in U.S. Pat. No. 5,578,563.

The, or each, first fragrance oil itself can comprise any perfume raw material suitable for use in fragrancing compositions. Overall, the fragrance oil will most often be liquid at ambient temperatures and consist of a single individual perfume raw material. A wide variety of chemicals are known for fragrance uses, including materials such as aldehydes, ketones and esters. However, naturally occurring plant and animal oils and exudates comprising complex mixtures of various chemical compositions are also commonly known for use as fragrances. The individual perfume raw materials which comprise a known natural oil can be found by reference to journals commonly used by those skilled in the art such as "Perfume and Flavourist" or "Journal of Essential Oil Research". In addition, some perfume raw materials are supplied by the fragrance houses as mixtures in the form of proprietary speciality accords.

In order that fragrance oils can be developed with the appropriate character for the present invention, the perfume raw materials have been classified based upon two key physical characteristics:

(i) boiling point (BP) measured at 1 atmosphere pressure. The boiling point of many fragrance materials are given in *Perfume and Flavour Chemicals (Aroma Chemicals)*, Steffen Arctander (1969). Perfume raw materials for use in the present invention are divided into volatile perfume raw materials (which have a boiling point of less than, or equal to, about 250° C.) and residual perfume raw materials (which have a boiling point of greater than about 250° C., preferably greater than about 275° C.). Volatile perfume raw materials, for the purposes of this invention, are considered to be those that impart "top note" i.e. light, fresh, fruity, citrus, green or delicate floral characters to the, or each, first fragrance oil and the like. Similarly, the residual perfume raw materials are considered to be those that impart "middle or base note" i.e. musk, sweet, balsamic, spicy, woody or heavy floral characters to the, or each, first fragrance oil and the like. All perfume raw materials will preferably have boiling points (BP) of about 500° C. or lower.

(ii) odour detection threshold which is defined as the lowest vapour concentration of that material which can be olfactorily detected. The odour detection threshold and some odour detection threshold values are discussed in, e.g., "Standardized Human Olfactory Thresholds", M. Devos et al, IRL Press at Oxford University Press, 1990, and "Compilation of Odor and Taste Threshold Values Data", F. A. Fazzalar, editor ASTM Data Series DS 48A, American Society for Testing and Materials, 1978, both of said publications being incorporated by reference. Perfume raw materials for use in the present invention can be classified as those with a low odour detection threshold of less than, or equal to, 50 parts per billion, preferably less than, or equal to, 10 parts per billion and those with a high odour detection threshold which are detectable at greater than 50 parts per billion (values as determined from the references above).

Since, in general, perfume raw materials refer to a single individual compound, their physical properties (such as ClogP, boiling point, odour detection threshold) can be found by referencing the texts cited above. In the case that the perfume raw material is a natural oil, which comprises a mixture of several compounds, the physical properties of the complete oil should be taken as the weighted average of the individual compounds. In the case that the perfume raw material is a proprietary speciality accord, its physical properties should be obtained from the supplier.

First fragrance oils for use in the first composition of the method described herein can comprise any mixture of known perfume raw materials such that the desired character, in particular a character that is desirable for the user to experience in periodic fragrance enhancements, is achieved. In general, a broad range of suitable perfume raw materials can be found in U.S. Pat. Nos. 4,145,184, 4,209,417, 4,515,705, and 4,152,272. Non-limiting examples of perfume raw materials which are useful for blending to formulate first fragrance oils for the present invention are given below. Any perfume raw materials, natural oils or proprietary speciality accords known to a person skilled in the art can be used within the present invention.

However, it is preferred that the at least one first fragrance oil of the first composition for use in the method described herein comprises about 5% or greater, preferably from about 5% to about 99%, more preferably from about 5% to about 70%, still more preferably from about 10% to about 60%, and even more preferably from about 25% to about 60%, by weight of the at least one first fragrance oil, of volatile "top note" perfume raw material(s) i.e., materials having a boiling point of less than, or equal to, about 250° C. It is preferred that the at least one first fragrance oil also comprises from about 0.01% to about 95%, preferably from about 5% to about 85%, more preferably from about 10% to about 60%, by weight of the at least one first fragrance oil, of the residual "middle and base note" perfume raw materials i.e., materials having a boiling point of greater than about 250° C. Furthermore, it is preferred that the weight ratio of volatile "top note" to residual "middle and base notes" perfume raw materials within the at least one first fragrance oil is in the range from about 1:20 to about 20:1, preferably from about 1:10 to about 10:1, more preferably from about 8:1 to about 1:2, most preferably from about 1.2:1 to about 1:1.2.

Furthermore, it is preferred that, within the at least one first fragrance oil, perfume raw materials are used which have a low odour detection threshold. It is preferred for use herein that the "top note" perfume raw materials within the at least one first fragrance oil comprise 5% or greater, by weight of the "top note" perfume raw materials, of "top note" perfume raw materials which have an odour detection level of less than, or equal to, 50 parts per billion, preferably less than, or equal to, 10 parts per billion. In addition, it is highly preferred that the "middle or base note" perfume raw materials within the at least one first fragrance oil comprise 10% or greater, more preferably 20% or greater and most preferably 50% or greater, by weight of the "middle or base note" raw materials, of "middle notes" or "base notes", or a mixture thereof, with an odour detection threshold of less than, or equal to, 50 parts per billion, preferably less than, or equal to, 10 parts per billion. Since materials with low odour detection levels can be detected when only very small levels are present, they are particularly useful for developing the long lasting character of the at least one first fragrance oil released over time from the complex with the at least one first cyclic oligosaccharide in the first composition.

Volatile perfume raw materials ("top notes") useful in the present invention are selected from, but are not limited to, aldehydes with a relative molecular mass of less than or equal to about 200, esters with a relative molecular mass of less than or equal to about 225, terpenes with a relative molecular mass of less than or equal to about 200, alcohols with a relative molecular mass of less than or equal to about 200, ketones with a relative molecular mass of less than or equal to about 200, nitriles, pyrazines, and mixtures thereof.

Examples of volatile "top note" perfume raw materials having a boiling point of less than, or equal to, 250° C., with a low odour detection are selected from, but are not limited to, anethol, methyl heptine carbonate, ethyl acetoacetate, para cymene, nerol, decyl aldehyde, para cresol, methyl phenyl carbinyl acetate, ionone alpha, ionone beta, undecylenic aldehyde, undecyl aldehyde, 2,6-nonadienal, nonyl aldehyde and octyl aldehyde. Further examples of volatile perfume raw materials having a boiling point of less than, or equal to, 250° C., which are generally known to have a low odour detection threshold include, but are not limited to, phenyl acetaldehyde, anisic aldehyde, benzyl acetone, ethyl-2-methyl butyrate, damascenone, damascone alpha, damascone beta, flor acetate, frutene, fructone, herbavert, iso cyclo citral, methyl isobutenyl tetrahydro pyran, isopropyl quinoline, 2,6-nonadien-1-ol, 2-methoxy-3-(2-methylpropyl)-pyrazine, methyl octine carbonate, tridecene-2-nitrile, allyl amyl glycolate, cyclogalbanate, cyclal C, melonal, gamma nonalactone and cis 1,3-oxathiane-2-methyl-4-propyl.

Other volatile "top note" perfume raw materials having a boiling point of less than, or equal to, 250° C., which are useful in the present invention, and which have a high odour detection threshold, are selected from, but are not limited to, benzaldehyde, benzyl acetate, camphor, carvone, borneol, bornyl acetate, decyl alcohol, eucalyptol, linalool, hexyl acetate, iso-amyl acetate, thymol, carvacrol, limonene, menthol, iso-amyl alcohol, phenyl ethyl alcohol, alpha pinene, alpha terpineol, citronellol, alpha thujone, benzyl alcohol, beta gamma hexenol, dimethyl benzyl carbinol, phenyl ethyl dimethyl carbinol, adoxal, allyl cyclohexane propionate, beta pinene, citral, citronellyl acetate, citronellal nitrile, dihydro myrcenol, geraniol, geranyl acetate, geranyl nitrile, hydroquinone dimethyl ether, hydroxycitronellal, linalyl acetate, phenyl acetaldehyde dimethyl acetal, phenyl propyl alcohol, prenyl acetate, triplal, tetrahydrolinalool, verdox and cis-3-hexenyl acetate.

Examples of residual "middle and base note" perfume raw materials having a boiling point of greater than 250° C., and which have a low odour detection threshold, are selected from, but are not limited to, ethyl methyl phenyl glycidate, ethyl vanillin, heliotropin, indol, methyl anthranilate, vanillin, amyl salicylate and coumarin. Further examples of residual perfume raw materials having a boiling point of greater than 250° C., and which are generally known to have a low odour detection threshold, include, but are not limited to, ambrox, bacdanol, benzyl salicylate, butyl anthranilate, cetalox, ebanol, cis-3-hexenyl salicylate, lilial, gamma undecalactone, gamma dodecalactone, gamma decalactone, calone, cymal, dihydro iso jasmonate, iso eugenol, lyral, methyl beta naphthyl ketone, beta naphthol methyl ether, para hydroxyl phenyl butanone, 8-cyclohexadecen-1-one, oxocyclohexadecen-2-one/habanolide, florhydral and intreleven aldehyde.

Other residual "middle and base note" perfume raw materials having a boiling point of greater than 250° C. which are useful in the present invention, and which have a high odour detection threshold, are selected from, but are not limited to, eugenol, amyl cinnamic aldehyde, hexyl cinnamic aldehyde, hexyl salicylate, methyl dihydro jasmonate, sandalore, veloutone, undecavertol, exaltolide/cyclopentadecanolide, zingerone, methyl cedrylone, sandela, dimethyl benzyl carbinyl butyrate, dimethyl benzyl carbinyl isobutyrate, triethyl citrate, cashmeran, phenoxy ethyl isobutyrate, iso eugenol acetate, helional, iso E super, ionone gamma methyl, pentalide, galaxolide and phenoxy ethyl propionate.

First Cyclic Oligosaccharides

The first composition for use in the method described herein preferably comprises from about 0.001% to about 40%, more preferably from about 0.1% to about 25%, still more preferably from about 1% to about 20%, even more preferably from about 0.5% to about 10%, and most preferably from about 2% to about 6%, by weight of the first composition, of the at least one first cyclic oligosaccharide.

As used herein, the term "cyclic oligosaccharide" means a cyclic structure comprising six or more saccharide units. Preferred for use herein are cyclic oligosaccharides having six, seven or eight saccharide units and mixtures thereof, more preferably six or seven saccharide units and mixtures thereof and even more preferably seven saccharide units and mixtures thereof. It is common in the art to abbreviate six, seven and eight membered cyclic oligosaccharides to α, β and γ respectively.

The at least one first cyclic oligosaccharide of the first composition used for the present invention may comprise any suitable saccharide or mixtures of saccharides. Examples of suitable saccharides include, but are not limited to, glucose, fructose, mannose, galactose, maltose and mixtures thereof. However, preferred for use herein are cyclic oligosaccharides of glucose. The preferred cyclic oligosaccharides for use herein are α-cyclodextrins or β-cyclodextrins, or mixtures thereof, and the most preferred cyclic oligosaccharides for use herein are β-cyclodextrins.

The first cyclic oligosaccharide, or mixture of cyclic first oligosaccharides, for use herein may be substituted by any suitable substituent or mixture of substituents. Herein, the use of the term "mixture of substituents" means that two or more different suitable substituents can be substituted onto one cyclic oligosaccharide. The derivatives of cyclodextrins consist mainly of molecules wherein some of the hydroxyl (OH) groups have been substituted. Suitable substituents include, but are not limited to, alkyl groups; hydroxyalkyl groups; dihydroxyalkyl groups; (hydroxyalkyl)alkylenyl bridging groups such as cyclodextrin glycerol ethers; aryl groups; maltosyl groups; allyl groups; benzyl groups; alkanoyl groups; cationic cyclodextrins such as those containing 2-hydroxy-3-(dimethylamino) propyl ether; quaternary ammonium groups; anionic cyclodextrins such as carboxyalkyl groups, sulphobutylether groups, sulphate groups, and succinylates; amphoteric cyclodextrins; and mixtures thereof. Other cyclodextrin derivatives are disclosed in copending U.S. application Ser. No. 09/32192 (May 27, 1999), which is incorporated herein by reference.

The substituents may be saturated or unsaturated, straight or branched chain moieties. Preferred substituents include saturated and straight chain alkyl groups, hydroxyalkyl groups and mixtures thereof. Preferred alkyl and hydroxyalkyl substituents are selected from C1–C8 alkyl or hydroxyalkyl groups or mixtures thereof, more preferred alkyl and hydroxyalkyl substituents are selected from C1–C6 alkyl or hydroxyalkyl groups or mixtures thereof, even more preferred alkyl and hydroxyalkyl substituents are selected from C1–C4 alkyl or hydroxyalkyl groups and mixtures thereof. Especially preferred alkyl and hydroxyalkyl substituents are propyl, hydroxypropyl, ethyl and methyl, more especially hydroxypropyl and methyl and even more preferably methyl.

Preferred first cyclic oligosaccharides for use in the present invention are unsubstituted, or are substituted by only saturated straight chain alkyl, or hydroxyalkyl, substituents. Therefore, preferred examples of first cyclic oligosaccharides for use herein are α-cyclodextrin, β-cyclodextrin, methyl-α-cyclodextrin, methyl-β-cyclodextrin, hydroxypropyl-α-cyclodextrin and hydroxypropyl-β-cyclodextrin, or mixtures thereof. Most preferred examples of first cyclic oligosaccharides for use herein are methyl-α-cyclodextrin and methyl-β-cyclodextrin. These are available from Wacker-Chemie GmbH, Hanns-Seidel-Platz 4, Munchen, Germany under the tradenames Alpha W6 M and Beta W7 M respectively. Especially preferred is methyl-β-cyclodextrin.

Methods of modifying first cyclic oligosaccharides are well known in the art. For example, see "Methods of Selective Modifications of Cyclodextrins" Chemical Reviews (1998) Vol. 98, No. 5, pp 1977–1996, Khan et al and U.S. Pat. No. 5,710,268.

In addition to identifying the preferred substituents themselves (as outlined above), it is also preferred that the first cyclic oligosaccharides for use in the present invention have an average degree of substitution of at least 1.6, wherein the term "degree of substitution" means the average number of substituents per saccharide unit. Preferred first cyclic oligosaccharides for use herein have an average degree of substitution of less than about 2.8. More preferably, the first cyclic oligosaccharides for use herein have an average degree of substitution of from about 1.7 to about 2.0. The average number of substituents can be determined using common Nuclear Magnetic Resonance techniques known in the art.

The first cyclic oligosaccharides used in the present invention are preferably soluble in the first solvent or the mixture thereof. As used herein, "soluble" means at least about 0.1 g of solute dissolves in 100 ml of the first solvent(s), at 25° C. and 1 atm of pressure. Preferably, the first solvent or the mixture thereof includes water. More preferably, the first cyclic oligosaccharides for use herein have a solubility of at least about 1 g/100 ml, at 25° C. and 1 atm of pressure. Preferred is that first cyclic oligosaccharides are only present at levels up to their solubility limits in a given first composition at room temperature (25° C.). A person skilled in the art will recognise that the levels of first cyclic oligosaccharides used in the present invention will also be dependent on the overall components of the first composition and their levels, for example the solvents used or the exact first fragrance oils, or combination of first fragrance oils, present in the first composition. Therefore, although the limits stated for the first cyclic oligosaccharides are preferred, they are not exhaustive.

First Solvent

The first solvent(s) has a dielectric constant at 25° C. of greater than or equal to 43 at normalised 0 Hz frequencies. A method of measuring dielectric constants and some dielectric constant values may be found in CRC Handbook of Chemistry and Physics, 66th Edition, 1985–1986, CRC Press. A dielectric constant of greater than or equal to 45 is preferred. Whilst not wishing to be bound by theory, it is believed that a dielectric constant of greater than or equal to 43 ensures that the complex of the at least one first fragrance oil and the at least one first cyclic oligosaccharide is sufficiently thermodynamically stable to be detectable in the first composition by methods such as nuclear magnetic resonance or the like.

The first composition for use in the method described herein preferably comprises at least about 40%, more preferably from about 60% to about 97%, and most preferably from about 80% to about 92%, by weight of the first composition, first solvent, preferably water.

The first composition for use in the method described herein can optionally comprise any suitable compatible solvent. However, it is important that, if any other solvent is incorporated into the first composition, it is present at a level such that the mixture of first solvents has a dielectric constant at 25° C. of greater than or equal to 43, preferably greater than or equal to 45, thereby ensuring that the stability of the first fragrance:first cyclic oligosaccharide complex is not compromised. As such, it is highly preferred that the minimum weight ratio of water to any other compatible solvent, within the first composition, is about 2.125:1.

Second Composition

Second Fragrance Oil

The second composition for use in the cosmetic method described herein preferably comprises from about 0.01% to about 99%, more preferably from about 0.25% to about 50%, still more preferably from about 0.5% to about 40%, even more preferably from about 1% to about 25%, and most preferably from about 2.5% to about 25%, by weight of the second composition, of at least one second fragrance oil.

The at least one second fragrance oil may be the same as, or different from, the at least one first fragrance oil.

As previously described within this application, the term "fragrance oil" relates to a perfume raw material, or mixture of perfume raw materials, that is/are used to impart an overall pleasant odour profile to a composition. In general, a broad range of suitable perfume raw materials can be found in U.S. Pat. Nos. 4,145,184, 4,209,417, 4,515,705, and 4,152,272. Non-limiting examples of perfume raw materials which are useful for blending to formulate second fragrance oil(s) for the present invention are those given above under the heading "First Fragrance Oil". In addition, any perfume raw materials, natural oils or proprietary speciality accords known to a person skilled in the art can be used as the at least one second fragrance oil.

The at least one second fragrance oil for use in the method of the present invention is preferably blended such that it contributes the desired characters to the background scent. As such, this fragrance can be developed by blending top, middle and base notes in the traditional way or, if second cyclic oligosaccharide(s) are present, by blending higher levels of top notes, and/or by using highly odiferous notes, to deliver fragrances with different characters. The perfume raw materials that are used to develop the at least one second fragrance oil for the second composition are selected based on the desired overall fragrance character combination.

Second Solvent

The second solvent, or the mixture thereof, is chosen to ensure that the at least one second fragrance oil is soluble therein—by the term "soluble" is meant that at least about 0.1 g solute dissolves in 100 ml second solvent(s) at 25° C. and 1 atm pressure. Alternatively, the second solvent or the mixture thereof is chosen to ensure that the at least one second fragrance oil is dispersed therein.

The second composition preferably comprises greater than about 50%, more preferably from about 55% to about 99.9%, most preferably from about 60% to about 95%, by weight of the second composition, of a second solvent or a mixture thereof.

It is preferred that the second solvent(s) includes at least one volatile solvent. As used herein, the term "volatile" refers to substances having a boiling point less than 1 atm, of less than about 95° C., even more preferably less than about 90° C., still more preferably less than about 85° C., most preferably less than about 80° C.

More preferably, the second solvent(s) substantially evaporate over from about 30 seconds to about 60 minutes at 25° C. after application to the surface. The term "substantially evaporate" as used herein means greater than 75% evaporation at 25° C. under 1 atm pressure. Greater than 90%, preferably greater than 95%, evaporation of the second solvent(s) desirably occurs over from about 30 seconds to about 60 minutes at 25° C. under 1 atm pressure, after application to the surface.

The second composition for use in the method described herein preferably comprises greater than about 50%, more preferably from about 55% to about 99.9%, even more preferably from about 60% to about 95%, by weight of the second composition, of a volatile solvent, or mixture of volatile solvents. Any volatile solvent having a boiling point, under 1 atm, of less than about 95° C. and suitable for use in the second composition can be used herein. The solvents for use herein are preferably organic, volatile, odourless, solvents.

Preferably, the volatile solvent(s) for use herein will be safe for use on a wide range of surfaces, more preferably on human or animal skin or hair. Suitable volatile solvents include, but are not limited to, those found in the *CTFA International Cosmetic Ingredient Dictionary and Handbook*, 7th edition, volume 2 P 1670–1672, edited by Wenninger and McEwen (*The Cosmetic, Toiletry, and Fragrance Association, Inc.*, Washington, D.C., 1997). Conventionally used volatile solvents include C3–C14 saturated and unsaturated, straight or branched chain hydrocarbons such as cyclohexane, hexane, isopentane, pentane, ethers such as diethyl ether; straight or branched chain alcohols and diols such as methanol, ethanol, isopropanol, t-butyl alcohol, butoxypropanol, isopentyldiol; aldehydes and ketones such as acetone; propellants, and mixtures thereof. Preferred volatile solvents are ethers such as diethyl ether; straight or branched chain alcohols and diols such as methanol, ethanol, isopropanol, t-butyl alcohol, butoxypropanol, isopentyldiol; propellants, and mixtures thereof. More preferred for use herein are C1–C4 straight chain or branched chain alcohols, for example, methanol, ethanol, isopropanol and t-butanol and mixtures thereof, and most preferred for use herein is ethanol.

The second solvent(s) for use in the method described herein may optionally include water. If present, the second composition will preferably comprise from about 0.1% to about 40%, more preferably from about 1% to about 30%, even more preferably about 5% to about 20%, by weight of the second composition, of water.

Second Cyclic Oligosaccharides

The second composition for use in the method described herein optionally comprises from about 0.1% to about 95%, preferably from about 0.5% to about 50%, more preferably from about 1% to about 25%, and most preferably from about 2% to about 8%, by weight of the second composition, of the at least one second cyclic oligosaccharide.

In the second composition, the at least one second cyclic oligosaccharide is not present in the form of a complex with the at least one second fragrance oil. This is achieved by selecting the second solvent, or the weight ratio of a mixture of second solvents, so that the second solvent or the mixture thereof has a dielectric constant at 25° C. of less than 43, preferably less than 41. The absence of such a complex can, for example, be determined by Nuclear Magnetic Resonance. However, when the second composition is applied to the surface, an association of the at least one second cyclic oligosaccharide and the at least one second fragrance oil, is formed, as is described hereinabove.

As already described, the term "cyclic oligosaccharide" means a cyclic structure comprising six or more saccharide units. Any cyclic oligosaccharide and substituted cyclic oligosaccharide that has already been described herein as being suitable as a first cyclic oligosaccharide for use in the first composition is also suitable as an optional second cyclic oligosaccharide for use in the second composition.

The second cyclic oligosaccharide(s) used for the present invention are preferably soluble in the second solvent, or mixture of second solvents, of the second composition. As used herein, "soluble" means at least about 0.1 g of solute dissolves in 100 ml of second solvent(s), at 25° C. and 1 atm of pressure. Preferably, the second cyclic oligosaccharides for use herein have a solubility of at least about 1 g/100 ml, at 25° C. and 1 atm of pressure.

Highly preferred examples of second cyclic oligosaccharides are α-cyclodextrin, β-cyclodextrin, methyl-α-cyclodextrin, methyl-β-cyclodextrin, hydroxypropyl-β-cyclodextrin and hydroxypropyl-β-cyclodextrin. Most preferred examples of second cyclic oligosaccharides for use herein are methyl-α-cyclodextrin and methyl-β-cyclodextrin. These are available from Wacker-Chemie GmbH Hanns-Seidel-Platz 4, Munchen, Germany under the tradenames Alpha W6 M and Beta W7 M respectively. Especially preferred is methyl-β-cyclodextrin.

When the second composition comprises at least one second cyclic oligosaccharide, it is highly preferred that the at least one second fragrance oil of the second composition comprises higher levels of top notes, and/or highly odiferous notes, to deliver fragrances with different characters, in the manner already described for the first fragrance oil of the first composition.

Nonvolatile Solvents

The first and second compositions for use in the method described herein may optionally comprise "nonvolatile" solvents having a boiling point, under 1 atm, greater than, or equal to, 95° C. Suitable non-volatile solvents include, but are not limited to, heptane, isooctane, toluene, xylene; halogenated alkanes such as perfluorodecalin; dimethyl ether, propanol, n-butyl alcohol, benzyl alcohol, butylene glycol, volatile silicones such as cyclomethicones, for example, octamethyl cyclo tetrasiloxane and decamethyl cyclopentane siloxane; volatile siloxanes such as phenyl pentamethyl disiloxane, phenylethylpentamethyl disiloxane, hexamethyl disiloxane, methoxy propylheptamethyl cyclotetrasiloxane, chloropropyl pentamethyl disiloxane, hydroxypropyl pentamethyl disiloxane, octamethyl cyclotetrasiloxane, and decamethyl cyclopentasiloxane benzyl benzoate, diethyl phthalate, isopropyl myristate, and mixtures thereof.

Molecular Wedges

The first and second compositions for use herein may optionally comprise at least one molecular wedge. While not wishing to be limited by theory, the above mentioned molecular wedge molecules can form tertiary inclusion complexes with the fragrance oil and the cyclic oligosaccharide. These small dipolar molecules can fit into the cavity of the cyclic oligosaccharide and anchor via their hydroxyl groups onto the outside rim of the cyclic oligosaccharide through hydrogen bonding. This enables the inclusion of all or parts of the fragrance oil into the cavity of the cyclic oligosaccharide such that the stability of the formed tertiary complex is increased versus the binary complex formed by the fragrance oil and cyclic oligosaccharide alone.

Low molecular weight polyol molecular wedges having from about 2 to about 12 carbon atoms, preferably from about 2 to about 6 carbon atoms, and at least one hydroxyl functional group, preferably at least 2 hydroxyl functional groups, are preferably used herein for further prolonging the fragrance character profile of the first composition, and/or the second composition if at least one second cyclic oligosaccharide is present therein. These polyols can further contain ether groups within the carbon chain. Suitable examples include ethylene glycol, propylene glycol, dipropylene glycol, 1,4-butanediol, 1,6-hexanediol and mixtures thereof. When present, these polyols are present at a level of from about 0.01% to about 20%, preferably from about 0.1% to about 10%, and especially from about 0.5% to about 5% by weight of the first composition, and/or the second composition if at least one second cyclic oligosaccharide is present therein. It is preferred that the molar ratio of molecular wedge material to cyclic oligosaccharide is from 10:1 to 1:10, preferably 1:1 or greater, especially about 1:1.

Synthetic Silicate Clays

It is preferred that the first and second compositions for use in the method described herein comprise from about 0.001% to about 15%, preferably from about 0.01% to about 10%, more preferably from about 0.05% to about 5% and even more preferably from about 0.1% to about 4%, by weight, of a synthetic silicate clay or mixture thereof. Any synthetic silicate clay which has a trioctahedral smectite structure and a particle size less than 25 nm is useful in the present invention. Preferred materials are hydrous sodium lithium magnesium silicate modified with tetra sodium pyrophosphate, hydrous sodium lithium magnesium fluoro-silicate and hydrous sodium lithium magnesium silicate, or a mixture thereof, all of which are available from Laporte Industries Ltd., Widnes, United Kingdom.

Other Optional Ingredients

The first and second compositions for use in the method described herein can contain a variety of other optional ingredients suitable for rendering such compositions more cosmetically or aesthetically acceptable or to provide them with additional usage benefits. Such conventional optional ingredients are well-known to those skilled in the art. These include any cosmetically acceptable ingredients such as those found in the *CTFA International Cosmetic Ingredient Dictionary and Handbook*, 7th edition, edited by Wenninger and McEwen, (*The Cosmetic, Toiletry, and Fragrance Association, Inc.*, Washington, D.C., 1997).

Such optional additional ingredients that are suitable for inclusion into the present compositions include, but are not limited to, alcohol denaturants such as denatonium benzoate; UV stabilisers such as benzophenone-2; antioxidants such as tocopheryl acetate; preservatives such as phenoxyethanol, benzyl alcohol, methyl paraben, propyl paraben; dyes; pH adjusting agents such as lactic acid, citric acid, sodium citrate, succinic acid, phosphoric acid, sodium hydroxide, sodium carbonate; deodorants and anti-microbials such as farnesol and zinc phenolsulphonate; humectants such as glycerine; oils; skin conditioning agents such as allantoin; cooling agents such as trimethyl isopropyl butanamide and menthol; hair conditioning ingredients such as panthenol, panthetine, pantotheine, panthenyl ethyl ether, and combinations thereof; silicones; solvents such as hexylene glycol; hair-hold polymers such as those described in WO-A-94/08557; salts in general, such as potassium acetate and sodium chloride and mixtures thereof. If present, these additional ingredients will preferably be present at a level of less than about 20%, more preferably less than about 10%, by weight, of the first or second composition. More preferably, these additional ingredients will be present at a level of less than about 5%, by weight, of the first or second composition.

Product Forms

The first and second compositions for use in the method described herein may take any form suitable for use, preferably for cosmetic use. These include, but are not limited to, vapour sprays, aerosols, emulsions, lotions, liquids, creams, gels, sticks, ointments, pastes, mousses and cosmetics (e.g., semi-solid or liquid make-up, including foundations). Preferably, the compositions take the form of a vapour spray.

The first and second compositions for use in the method described herein will preferably comprise an acceptable carrier. The phrase "acceptable carrier", as used herein, means one or more compatible solid or liquid fillers, diluents, extenders and the like, which are acceptable as defined hereinabove. The term "compatible", as used herein, means that the components of the first and second compositions are capable of being combined with the required and optional components of the first and second compositions outlined above, and with each other, in a manner such that there is no interaction which would substantially reduce the efficacy of the first and second compositions under ordinary use situations. The type of carrier utilised in the present invention depends on the type of product desired and may comprise, but is not limited to, solutions, aerosols, emulsions (including oil-in-water or water-in-oil), gels, solids and liposomes.

Delivery Package

According to the present invention there is also provided a delivery package suitable for use in the method of the present invention, the package comprising at least first and second chambers, the first chamber containing, in use, a first composition and the second chamber containing, in use, a second composition wherein the package is adapted to separately dispense the first and second compositions either simultaneously or sequentially. In a preferred embodiment, the package comprises a first nozzle in fluid communication with the first chamber and a second nozzle in fluid communication with the second chamber so that, in use, the first and second compositions can be applied simultaneously. This package can be further enhanced by having one or more further chambers in addition to the first and second chambers, wherein each further chamber contains, in use, a different first or second composition. The package can be still further enhanced by adapting the package to dispense at least one first composition and at least one second composition either simultaneously or sequentially by, for example, use of a manual control such as a dial. As such, the consumer would be able to customise the fragrance combination delivered. Furthermore, each chamber could be supplied individually as a refill cartridge so that the consumer can replace the composition(s), thus having even further choice over the fragrance combination delivered.

Kit

According to this invention there is also provided a kit suitable for use in the method described herein, the kit comprising:

a) a first composition comprising:

i) at least one first fragrance oil;

ii) at least one first cyclic oligosaccharide, wherein the at least one first fragrance oil and the at least one first cyclic oligosaccharide form a complex, which complex is dissolved or dispersed in the first composition; and iii) a first solvent, or a mixture thereof, wherein the first solvent or the mixture thereof has a dielectric constant at 25° C. of greater than or equal to 43, preferably greater than or equal to 45;

b) a second composition comprising:

i) at least one second fragrance oil; and ii) a second solvent, or a mixture thereof, wherein the at least one second fragrance oil is soluble or is dispersed at 25° C. in the second solvent or the mixture thereof; and c) usage instructions directing the user as to how to use the first and second compositions in the method.

It is possible that either the first and/or second compositions of this kit could be supplied in a series of different varieties such that, for example, the same second composition can be used with differing first compositions (or vice versa) to customise the overall fragrance character combination. Furthermore, one or more of the first or second compositions of the kit of the present invention can be reapplied over time such that the overall fragrance character can be enhanced or altered over time.

Preparation of First and Second Compositions

First and second compositions for use in the present invention should be prepared according to procedures usually used in fragrance delivery and that are well known and understood by those skilled in the art. The complexing of the perfume raw materials of the first composition, or optionally of the second composition, can occur at any reasonable stage in the preparation of either composition. As such, the at least one fragrance oil of either composition, or both compositions, can be prepared in its entirety, then combined with a suitable cyclic oligosaccharide(s) before addition to the remainder of either composition. Alternatively, the cyclic oligosaccharide(s) can be added to the first composition or optionally to the second composition prior to addition of the complete fragrance oil. Finally, it is possible to blend any single perfume raw material, or group of perfume raw materials, individually before either adding these to the balance of the fragrance oil for either the first or second compositions or to the balance of either of the first or second compositions.

All documents cited are, in relevant part, incorporated herein by reference; the citation of any document is not to be construed as an admission that it is prior art with respect to the present invention.

EXAMPLES

The following examples further illustrate the preferred embodiments within the scope of the present invention. These examples are given solely for the purposes of illustration and are not to be construed as limitations of the present invention as many variations of the invention are possible without departing from its spirit or scope. Unless otherwise indicated, all ingredients are expressed on a weight percentage of the active ingredient.

First Fragrance Oil Examples (I–VI) - for use in the first compositions

| Perfume Raw Materials | I (%) | II (%) | III (%) | IV (%) | V (%) | VI (%) |
|---|---|---|---|---|---|---|
| Decyl aldehyde | 0.80 | — | — | — | — | 0.05 |
| Melonal | 0.80 | 2.00 | — | — | 0.20 | 0.10 |
| Beta gamma hexenol | 1.00 | — | 0.55 | 0.50 | 0.20 | 0.20 |
| Cis 3 hexenyl acetate | 0.20 | — | 0.20 | 1.00 | — | 0.20 |
| Prenyl acetate | 4.00 | 1.00 | 0.75 | 0.30 | 2.00 | 2.00 |
| Methyl phenyl carbinyl acetate | 1.00 | — | — | 0.20 | — | — |
| Linalool | 4.00 | — | — | 5.00 | 7.00 | 3.00 |
| Cassis Base 345 - L 1 | 20.00 | 35.00 | — | — | — | — |
| Ethyl-2-methyl butyrate | 0.50 | — | 0.50 | 0.50 | 0.50 | — |
| Alpha damascone | 1.00 | 2.00 | — | 0.30 | — | — |
| Alpha Ionone | 6.00 | 4.00 | — | 0.50 | 0.50 | 1.00 |
| Indol, 10% in Diethyl Phthalate | 0.05 | — | — | — | — | — |
| Beta Damascone | 0.50 | — | — | — | 0.50 | 1.00 |
| P.T. Bucinal | 1.40 | — | — | 20.00 | 10.00 | 10.00 |
| Clove Bud Oil | 0.15 | — | — | — | 0.50 | 1.00 |
| Gamma decalactone | 3.00 | 2.50 | — | — | 0.20 | 0.10 |
| Undecalactone | 1.00 | — | — | 1.00 | 1.00 | 0.50 |
| Habanolide 100% 1 | 3.20 | 1.00 | 5.00 | 11.00 | 20.00 | 15.00 |
| Phenoxy ethyl isobutyrate | 0.50 | 0.50 | — | 0.60 | 4.00 | 2.00 |
| Cetalox | 2.40 | 0.30 | — | — | 0.20 | 0.40 |
| Ethyl vanillin 10% in benzyl salicylate | 1.20 | 2.50 | — | — | 2.00 | 2.00 |
| Methyl dihydro Jasmonate | 2.30 | 4.55 | 7.50 | 26.00 | 15.00 | 20.00 |
| Bergamot Oil | 15.00 | 10.30 | 11.00 | — | 5.00 | 7.00 |
| Prunella 1 | 30.00 | 13.00 | — | — | — | — |
| Cis-3-hexenyl salicyclate | — | 12.00 | 17.00 | — | — | 1.00 |
| Cyclo galbanate | — | 3.00 | 5.85 | — | — | 0.10 |
| Liffarome 1 | — | 0.60 | 1.40 | 0.10 | 0.10 | — |
| Vertocitral | — | 0.60 | 1.40 | — | — | 0.05 |
| Spearmint oil | — | 0.75 | 1.40 | — | — | — |
| Bourgeonal 3 | — | 3.65 | 2.65 | 1.50 | 1.50 | 1.50 |
| Citronellal nitrile | — | 0.75 | — | — | — | 0.30 |
| Dihydro mycenol | — | — | 32.00 | — | 2.00 | 10.00 |
| Lyral | — | — | 7.50 | 12.00 | — | — |
| Phenyl ethyl alcohol | — | — | 2.00 | 6.00 | 6.00 | — |
| 4-t-butyl cyclohexyl acetate | — | — | 1.30 | — | 2.55 | 2.00 |
| Ionone beta | — | — | 2.00 | — | 2.00 | 0.20 |
| Benzyl salicylate | — | — | — | 12.00 | 12.00 | 12.00 |
| Ylang Ylang Oil | — | — | — | 1.50 | — | 2.00 |
| Ethyl maltol | — | — | — | — | 0.05 | — |
| Orange oil, cold pressed | — | — | — | — | 2.00 | — |
| Methyl cedrylone | — | — | — | — | 3.00 | 5.00 |
| Veramoss 2 | — | — | — | — | — | 0.30 |

Second Fragrance Oil Examples (VII–XIII) - for use in the second compositions

| Perfume Raw Material | VII (%) | VIII (%) | IX (%) | X (%) | XI (%) | XII (%) | XIII (%) |
|---|---|---|---|---|---|---|---|
| Damascone beta | 0.1 | — | — | 1.9 | — | — | — |
| Allyl amyl glycolate | 0.1 | — | — | — | — | 0.2 | 0.3 |
| Ionone beta | 3 | 2.5 | — | — | — | — | — |
| Damascone alpha | — | 0.1 | 0.1 | 2.6 | 0.2 | 0.2 | 0.2 |
| Methyl phenyl carbinyl acetate | — | 1.7 | — | — | — | 0.4 | — |
| Cyclogalbanate 4 | — | — | 1.8 | — | — | — | 0.5 |
| Rose oxide | — | — | 0.3 | — | — | — | 0.1 |
| Ethyl-2-methyl butyrate | — | — | 0.1 | — | — | — | 0.1 |
| Fructone | 0.5 | — | 2.2 | — | 0.1 | — | 0.8 |
| Flor acetate | 1 | — | 6.5 | — | — | — | 2.1 |
| Ionone alpha | 0.5 | — | 3 | 3 | 0.2 | — | 1.1 |
| Melonal | — | — | — | 1.5 | 0.3 | — | — |
| Undecylenic aldehyde | — | — | — | — | — | 0.4 | — |
| Lemon Oil, Cold Pressed | 35 | 5 | — | — | — | 0.5 | — |
| Bergamot Oil, Eco Essence | 30 | — | — | 14.5 | — | 1.5 | — |
| Cassis Base 345-L 1 | 1 | — | — | 30 | 3 | 1.0 | — |
| Menthol | 0.5 | — | — | — | — | — | — |
| Beta gamma hexenol | 0.5 | 1 | 0.6 | — | — | — | — |
| Phenyl ethyl alcohol | 2 | — | 8 | — | 0.4 | 2.5 | — |
| Phenoxy ethyl propionate | — | — | — | — | 0.6 | — | — |
| Linalool | 8 | 5 | — | — | — | 1.5 | — |
| Cis-3-hexenyl acetate | — | 0.2 | — | — | — | — | — |
| Linalyl acetate | — | 5 | — | — | — | 1.2 | — |
| Dihydro myrcenol | — | 2 | 22 | — | — | — | — |
| Citronellol | — | 10 | — | — | — | 1.5 | — |
| Benzyl acetate | — | 6 | — | — | — | 4 | — |
| Verdox | — | — | 7 | — | — | — | — |
| Triplal | — | — | 0.6 | — | — | 0.2 | — |
| Alpha terpineol | — | — | — | — | — | 1.2 | — |
| Dihydro iso jasmonate | 3.5 | 15 | — | 0.2 | — | 2 | 5 |
| Cetalox 1 | 0.5 | 0.2 | 0.3 | 2.2 | — | 0.1 | — |
| Bacdanol 2 | 0.1 | — | 1.5 | — | — | — | 1 |
| Undecalactone | 1 | 2 | 2 | — | — | 10.3 | 1 |
| Lyral 2 | 8 | 15 | 17 | — | 10 | 2 | 10 |
| Florhydral 5 | — | — | — | — | 5 | — | 2 |
| Cis-3-hexenyl salicylate | — | 2 | — | — | — | 1.2 | 2 |
| Indol | — | — | — | — | 0.5 | 0.5 | — |
| Ethyl vanillin | — | 0.8 | 0.7 | 1.3 | — | — | — |
| Heliotropin | — | — | — | — | — | 0.5 | 1.6 |
| Ebanol 5 | — | 2.0 | — | — | — | — | — |
| Gamma decalactone | — | — | — | 4.5 | 0.4 | — | — |
| Prunella 1 | — | — | — | 35.5 | 4 | — | — |
| Lilial 5 | — | — | — | 0.7 | — | 15 | 10 |
| Benzyl salicylate | — | — | — | — | 20 | 20 | 10 |
| Habanolide 100% 1 | — | 8 | 11 | 1.5 | 10 | 0.2 | 15 |
| Roselea 2 | — | — | — | 0.6 | — | — | 5 |
| Exaltolide | 2.5 | 8 | 14 | — | 12 | 0.4 | 8 |
| Hexyl cinnamic aldehyde | 2.2 | 5 | — | — | 5 | 2 | — |
| Zingerone 5 | — | 0.5 | — | — | 0.8 | — | — |
| Methyl cedrylone | — | 3 | — | — | 17 | — | 4 |
| Eugenol | — | — | 1.3 | — | — | — | 0.2 |
| Sandela 5 | — | — | — | — | — | 10 | 5 |
| Methyl dihydro jasmonate | — | — | — | — | 10 | 10 | 15 |
| Ionone gamma methyl | — | — | — | — | — | 10 | — |

1. Firmenich SA, 1 Route des Jeunes, CH-1211 Geneva 8 SWITZERLAND
2. International Flavors & Fragrances 521 W. 57th St, New York, NY 10019 USA
3. Quest International, Ashford, Kent, TN24 OLT, United Kingdom
4. Dragoco Gerberding & Co AG, D-37601 Holzminden GERMANY
5. Givaudan-Roure, 19–23 voie des Bans BP98, 95101 Argenteuil Cedex, FRANCE Fragrance oil examples I–XIII were made by mixing the stated levels of each raw material at room temperature (25° C).

First and Second Compositions for Use in the Method - Examples XIV–XIX

| Example | XIV | | XV | | XVI | |
|---|---|---|---|---|---|---|
| Composition | 1st | 2nd | 1st | 2nd | 1st | 2nd |
| Fragrance | 5 | 10 | 2 | 12.5 | 0.6 | 15 |
| Cyclic Oligosaccharide 6 | 26 | 2.5 | 10 | 5 | 3 | 10 |
| Ethanol | 15 | 71.75 | 0 | 67.97 | 0 | 63.5 |
| Deionised Water | 52 | 15.75 | 88 | 12.53 | 93.9 | 11.5 |
| Laponite 7 | 2 | 0 | 0 | 2 | 2.5 | 0 |

| Example | XVII | | XVIII | | XIX | |
|---|---|---|---|---|---|---|
| Composition | 1st | 2nd | 1st | 2nd | 1st | 2nd |
| Fragrance | 1 | 8 | 1.5 | 11 | 2.5 | 14 |
| Cyclic Oligosaccharide 6 | 5 | 3 | 7.5 | 4 | 12.7 | 6 |
| Ethanol | 0 | 74.3 | 0 | 71.8 | 0 | 67.5 |
| Deionised Water | 92.5 | 13.7 | 89 | 13.2 | 84.8 | 12.5 |
| Laponite 7 | 1.5 | 1 | 2 | 0 | 0 | 0 |

6. Beta W7 M available from Wacker-Chemie GmbH, Hanns-Seidel-Platz 4, Munchen, Germany
7. Available from Laporte Industries Ltd., Widnes, United Kingdom The first composition (examples XIV to XIX left hand column) for each example was prepared as follows. The Laponite (if applicable) was dissolved in water at room temperature. The cyclic oligosaccharide was then added, followed by the fragrance oil and the ethanol (if applicable) with stirring. Any of the fragrance oils suitable for use in the first composition (i.e. any of fragrance oil examples I–VI) can be used when preparing any of the first compositions.

The second composition (examples XIV to XIX—right hand column) for each example was prepared as follows. The Laponite (if applicable) was dissolved in water at room temperature. The cyclic oligosaccharide was dissolved in ethanol at room temperature. The fragrance oil and water were added with stirring. Any of the fragrance oils suitable for use in the second composition (i.e. any of fragrance oil examples VII–XIII) can be used when preparing any of the second compositions.

Compositions were then packed in suitable packaging (kit or at least dual chamber delivery package as desired) and used according to the method, described herein. When the compositions of these examples were used according to the method, a new and long lasting fragrance character combination, particularly light, fresh, fruity, citrus, green or delicate floral "top note" fragrance character from the first composition, in combination with a balancing second fragrance character, was perceived as a fragrance character combination throughout usage. In addition, the user was able to experience noticeable enhancements of fragrance release throughout usage.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A method of applying a fragrance to a surface wherein the method comprises:
   a) applying to an area of the surface a first composition wherein the first composition comprises:
      i) at least one first fragrance oil;
      ii) at least one first cyclic oligosaccharide, wherein the first fragrance oil and the first cyclic oligosaccharide form a complex, which complex is dissolved or dispersed in the first composition; and
      iii) a first solvent, wherein the first solvent has a dielectric constant at 25° C. of greater than or equal to 43;
   b) simultaneously or sequentially, applying to the area or an area adjacent thereto a second composition wherein the second composition comprises:
      i) at least one second fragrance oil;
      ii) a second solvent, wherein the second fragrance oil is soluble or is dispersed at 25° C. in the second solvent; and
      iii) from about 0.1% to about 95%, by weight of the second composition, of at least one second cyclic oligosaccharide wherein said second cyclic oligosaccharide and said second fragrance oil do not form a complex;

wherein the application of the second composition can be applied before or after the first composition to an area and wherein the first solvent and the second solvent have a composite dielectric constant, at 25° C., of greater than or equal to 43.

2. A method according to claim 1 wherein the weight ratio of the first composition to the second composition upon application is from about 1:99 to 99:1.

3. A method according to claim 1 wherein to first composition comprises from about 0.001% to about 20%, by weight of the first composition, of the first fragrance oil.

4. A method according to claim 1 wherein the first fragrance oil comprises from about 5% or greater, by weight of the first fragrance oil, of a top note perfume raw material, or mixture of top note perfume raw materials, and wherein the top note perfume raw material has a boiling point of less than, or equal to, about 250° C. at 1 atmosphere pressure.

5. A method according to claim 1 wherein the top note perfume raw material of the first fragrance oil comprises 5% or greater, by weight of the top note perfume raw materials, of top note perfume raw materials which have an odour detection threshold of less than or equal to 50 parts per billion.

6. A method according to claim 1 wherein the first fragrance oil comprises from about 0.01% to about 95%, by weight of the first fragrance oil, of middle and base note perfume raw materials, wherein the middle and base note perfume raw materials are selected from perfume raw materials having a boiling point of greater than about 250° C. at 1 atmosphere pressure.

7. A method according to claim 1 wherein the middle or base note perfume raw materials of the first fragrance oil comprise 10% or greater, by weight of the first composition middle and base note perfume raw materials, of middle or base note perfume raw materials which have an odour detection threshold of less than or equal to 50 parts per billion.

8. A method according to claim 1 wherein, within the first fragrance oil, the weight ratio of top note perfume raw materials to middle or base note perfume raw materials is in the range from about 1:20 to about 20:1.

9. A method according to claim 1 wherein the first composition comprises at least about 40%, by weight of the first composition, of the first solvent wherein the first solvent is water.

10. A method according to claim 1 wherein the second composition comprises from about 0.01% to about 99%, by weight of the second composition, of at least one second fragrance oil.

11. A method according to claim 1 wherein the second composition comprises at least about 50%, by weight of the second composition, of a second solvent.

12. A method according to claim 11 wherein the second solvent comprises a volatile solvent, having a boiling point, less than 1 atm, of less than about 95° C.

13. A method according to claim 12 wherein the volatile solvent of the second composition is selected from the group consisting of $C_3$–$C_{14}$ saturated or unsaturated, straight or branched chain hydrocarbons, ethers, straight or branched chain alcohols, straight or branched chain diols, aldehydes, ketones, propellants, and mixtures thereof.

14. A method according to claim 13 wherein the volatile solvent of the second composition is a straight chain alcohol.

15. A method according to claim 1 wherein the first composition comprises from about 0.001% to about 40%, by weight of the first composition, of the first cyclic oligasaccharide.

16. A method according to claim 1 wherein the first or second cyclic oligosaccharide has six, seven or eight saccharide units and mixtures thereof.

17. A method according to claim 16 wherein the first or second cyclic oligosaccharide is a cyclodextrin.

18. A method according to claim 17 wherein the first or second cyclic oligosaccharide is substituted with a substituent selected from the group consisting of $C_1$–$C_8$ alkyl groups, $C_1$–$C_8$ hydroxyalkyl groups, and mixtures thereof.

19. A method according to claim 18 wherein the first or second cyclic oligosaccharide is substituted with alkyl groups.

20. A method according to claim 19 wherein said first or second cyclic oligosaccharide is selected from the group consisting of α-cyclodextrin, β-cyclodextrin, hydroxypropyl-α-cyclodextrin, hydroxypropyl-β-cyclodextrin, methyl-α-cyclodextrin, methyl-β-cyclodextrin and mixtures thereof.

21. A method according to claim 1 wherein the first solvent comprises water and any compatible solvent and wherein the minimum weight ratio of water to said compatible solvent, within the first composition, is about 2.125:1.

22. A method according to claim 1 wherein either, or both, of the first composition and the second composition, comprise from about 0.001% to about 15%, by weight, of a synthetic silicate clay.

23. A method according to claim 22 wherein the synthetic silicate clay is selected from the group consisting of hydrous sodium lithium magnesium silicate modified with tetra sodium pyrophosphate, hydrous sodium lithium magnesium fluoro-silicate, hydrous sodium lithium magnesium silicate and mixtures thereof.

24. A method according to claim 1, wherein the surface is a surface of the human or animal body.

* * * * *